US008666491B2

(12) United States Patent
Chen et al.

(10) Patent No.: US 8,666,491 B2
(45) Date of Patent: Mar. 4, 2014

(54) MEDICAL TELEMETRY SYSTEM WITH PRINTED CIRCUIT BOARD COMMUNICATION COIL

(75) Inventors: Joey Chen, Pasadena, CA (US); Daniel Aghassian, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 560 days.

(21) Appl. No.: 12/040,699

(22) Filed: Feb. 29, 2008

(65) Prior Publication Data

US 2009/0222066 A1 Sep. 3, 2009

(51) Int. Cl.
*A61N 1/375* (2006.01)
(52) U.S. Cl.
USPC .................................. 607/32; 607/60; 607/36
(58) Field of Classification Search
USPC ........................................ 607/32, 60, 62, 156
See application file for complete search history.

(56) References Cited

U.S. PATENT DOCUMENTS

| | | | |
|---|---|---|---|
| 5,948,006 A | 9/1999 | Mann | |
| 5,973,611 A | 10/1999 | Kulha et al. | 340/825.31 |
| 6,298,271 B1 * | 10/2001 | Weijand | 607/60 |
| 6,510,345 B1 * | 1/2003 | Van Bentem | 607/60 |
| 7,191,013 B1 | 3/2007 | Miranda et al. | |
| 2004/0230247 A1 * | 11/2004 | Stein et al. | 607/32 |
| 2006/0227989 A1 * | 10/2006 | Polinske | 381/322 |
| 2007/0060980 A1 | 3/2007 | Strother et al. | |
| 2007/0103617 A1 * | 5/2007 | Kitajima et al. | 349/58 |
| 2008/0046034 A1 | 2/2008 | Ibrahim | |
| 2009/0216068 A1 * | 8/2009 | Thomas et al. | 600/14 |

FOREIGN PATENT DOCUMENTS

| | | | |
|---|---|---|---|
| GB | 2333062 | 7/1999 | |
| JP | 2006066829 | 9/2006 | |
| WO | 2004002572 A1 | 1/2004 | |
| WO | 2006/110231 | 10/2006 | G07C 9/00 |
| WO | 2007/073507 | 6/2007 | H01Q 1/32 |

OTHER PUBLICATIONS

Internet Article; "Radio-frequency identification—Wikipedia, the free encyclopedia;" located at http://en.wikipedia.org/wiki/RFID; 27 pages.
Internet Article; "What is RFID?—iStart Technology in Business;" located at http://www.istart.co.nz/index/HM20/PC0/PV21902/EX245/AR28128.

(Continued)

*Primary Examiner* — Kennedy Schaetzle
*Assistant Examiner* — Erica Lee
(74) *Attorney, Agent, or Firm* — Wong, Cabello, Lutsch, Rutherford & Brucculeri, LLP.

(57) ABSTRACT

Disclosed is an improved external controller useable in an implantable medical device system. The communication coil in the external controller is formed in a printed circuit board (PCB), i.e., by using the various tracing layers and vias of the PCB. As illustrated, the PCB coil is formed at a plurality of trace layers in the PCB, and comprises a plurality of turns at some or all of the layers. The communication coil may wrap around the other circuitry used in the external controller, which circuitry may be mounted to the front and/or back of the PCB. The geometry of the coil is specially tailored to maximize its inductance, and hence maximize its ability to communicate in the sub-4 MHz range which is not significantly attenuated by the human body.

7 Claims, 6 Drawing Sheets

(56) References Cited

OTHER PUBLICATIONS

Internet Article; "Remote keyless entry (RKE) system;" located at http://www.electronics-manufacturers.com/info/rf/microwave-electronics/remote-keyless-entry-rke-system.html.

Internet Article; "Avante International Technology, Inc.—Reliable RFID Key Fob;" located at http://www.avantetech.com/products/keyfob/rfidkeyfob/.

Internet Article; "Fast Start-Up Oscillator (FOX) Boosts Superhet Performance—Maxim;" located at http://www.maxim-ic.com/appnotes.cfm/appnote_number/1955/ (Mar. 5, 2003).

Internet Article; "Discussion of Human Body RF Interaction;" located at http://www.connect802.com/human_body_rf.htm.

S.Y.Y. Leung et al., "Printed Polymer Based RFID Antenna on Curvilinear Surface," International Conference on Electronic Materials and Packaging 2006, 1-6 (Dec. 2006).

International Search Report and Written Opinion of the International Searching Authority regarding corresponding application No. PCT/US2008/084267 dated May 25, 2009.

* cited by examiner

MEDICAL TELEMETRY SYSTEM WITH PRINTED CIRCUIT BOARD COMMUNICATION COIL

FIELD OF THE INVENTION

The present invention relates to an improved external controller having particular applicability to implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

Portions of an IPG system are shown in FIG. 2 in cross section, and include the IPG 100 and an external controller 12. The IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from the external controller 12; and a charging coil 18 for charging or recharging the IPG's power source or battery 26 using an external charger (not shown). The telemetry coil 13 can be mounted within the header connector 36 as shown.

As just noted, an external controller 12, such as a hand-held programmer or a clinician's programmer, is used to wirelessly send data to and receive data from the IPG 100. For example, the external controller 12 can send programming data to the IPG 100 to set the therapy the IPG 100 will provide to the patient. Also, the external controller 12 can act as a receiver of data from the IPG 100, such as various data reporting on the IPG's status.

The communication of data to and from the external controller 12 occurs via magnetic inductive coupling. When data is to be sent from the external controller 12 to the IPG 100, coil 17 is energized with an alternating current (AC). Such energizing of the coil 17 to transfer data can occur using a Frequency Shift Keying (FSK) protocol for example, such as disclosed in U.S. patent application Ser. No. 11/780,369, filed Jul. 19, 2007, which is incorporated herein by reference in its entirety. Energizing the coil 17 induces an electromagnetic field, which in turn induces a current in the IPG's telemetry coil 13, which current can then be demodulated to recover the original data. Such data is typically communicated at a frequency of about 125 kHz, which in an FSK protocol might be 121 kHz for a logical '0' and 129 kHz for a logical '1'. As is well known, inductive transmission of data occurs transcutaneously, i.e., through the patient's tissue 25, making it particularly useful in a medical implantable device system.

A typical external controller 12 is shown in further detail in FIGS. 3 and 4A-4C. FIG. 3 shows a plan view of the external controller, including its user interface. The user interface generally allows the user to telemeter data (such as a new therapy program) from the external controller 12 to the IPG 100 or to monitor various forms of status feedback from the IPG for example. The user interface is somewhat similar to a cell phone or to other external controllers used in the art, and includes typical features such as a display 265, an enter or select button 270, and menu navigation buttons 272. Soft keys 278 can be used to select various functions, which functions will vary depending on the status of the menu options available at any given time. A speaker is also included within the housing 215 to provide audio cues to the user (not shown). Alternative, a vibration motor can provide feedback for users with hearing impairments.

FIGS. 4A-4C show various views of the external controller 12 with its outer housing 215 removed. Visible on the underside of the main printed circuit board (PCB) 120 is a battery 126 that provides power to the external controller 12. The battery 126 may be rechargeable via a power port 280 (FIG. 3) coupleable AC power source 292 (e.g., a wall plug), or may comprise a non-rechargeable battery. If the external controller 12 contains no battery 126, power port 280 would be used as the exclusive means for powering the device. A data port 282 (FIG. 3) is provided to allow the external controller 210 to communicate with other devices such as a computer 295. Such a data port 282 is useful for example to share data with another machine, to allow the external controller 210 to receive software updates, or to allow the external programmer 210 to receive a starter therapy program from a clinician programmer. An unlock button 281, recessed into the side of the housing, can be used to unlock the keys and buttons, and can be activated by pressing and holding that button for some duration of time (e.g., one second).

As alluded to earlier, FIGS. 4A-4C show the electronics within the housing 215 of the external controller 12. As can be seen from the various views, the electronics are generally supported by PCB 120. In the illustrated example, the front of the PCB 120 (FIG. 4A) includes the display 265 and the switches 122 which interact with the various buttons present on the housing 215 (see FIG. 3). The back of the PCB (FIG. 4B) includes the battery 126 and the data coil 17. In this embodiment, the back contains much of the circuitry (e.g., integrated circuits, capacitors, resistors, etc.) necessary for the external controller 12 to function. For example, the external controller 12's main microcontroller would reside on the back side of the PCB 120. However, this in not strictly necessary, and circuitry could also appear on the front of the PCB 120 or elsewhere.

Of particular concern to manufacturers of external controllers 12 is the data coil 17. As one skilled in the art will appreciate, the coil 17 is generally difficult and expensive to manufacture. Coils 17 are typically formed out of insulated strands of solid or stranded copper wire. Such wire is wound around a preformed shaped called a mandril to form the coil 17. It is important to precisely wind the coil 17 with the correct number of turns, such that the correct resistance and inductance of the coil is achieved. Once wound, the coil 17 is then typically bonded together with an adhesive to prevent it from unraveling. Depending on the type of insulation used, solvent or heat application can also assist in the bonding of the wires. The end terminals of the wire then must be stripped to verify inductance and resistance, and to check for shorted turns resulting from damage to the wire's insulation during winding. The finished coil is then attached to the PCB 120 with adhesive, and the terminals soldered to the PCB. If necessary, the coil 17 may require special mounting structure to elevate the coil above the underlying circuitry on the PCB 120, as best shown in the side view of FIG. 4C. Even if successfully manufactured and mounted to the PCB 120, the coil 17 remains a reliability concern, due to its susceptibility to mechanical shock, vibration, temperature fluctuations, and/or humidity. Additionally, the sheer bulk of the coil 17 adds to the overall size of the external controller 12, which is not desirable. This disclosure provides embodiments of a solution to mitigate shortcoming related to the manufacturing and reliability of the communication coil in the external controller.

DETAILED DESCRIPTION

The description that follows relates to use of the invention within a spinal cord stimulation (SCS) system. However, the invention is not so limited. Rather, the invention may be used with any type of implantable medical device system that could benefit from improved design for an external device which communicates with an implantable device. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

Disclosed is an improved external controller useable in an implantable medical device system. The communication coil in the external controller is formed in a printed circuit board (PCB), i.e., by using the various tracing layers and vias of the PCB. As illustrated, the PCB coil is formed at a plurality of trace layers in the PCB, and comprises a plurality of turns at some or all of the layers. The communication coil may wrap around the other circuitry used in the external controller, which circuitry may be mounted to the front and/or back of the PCB. The geometry of the coil is specially tailored to maximize its inductance, and hence maximize its ability to communicate in the sub-4 MHz range which is not significantly attenuated by the human body.

Figure 1B:
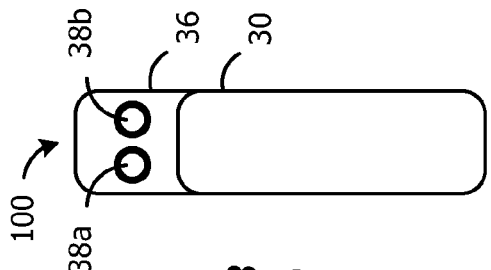
FIGS. 1A and 1B show an implantable pulse generator (IPG), and the manner in which an electrode array is coupled to the IPG in accordance with the prior art.
Figure 1A:
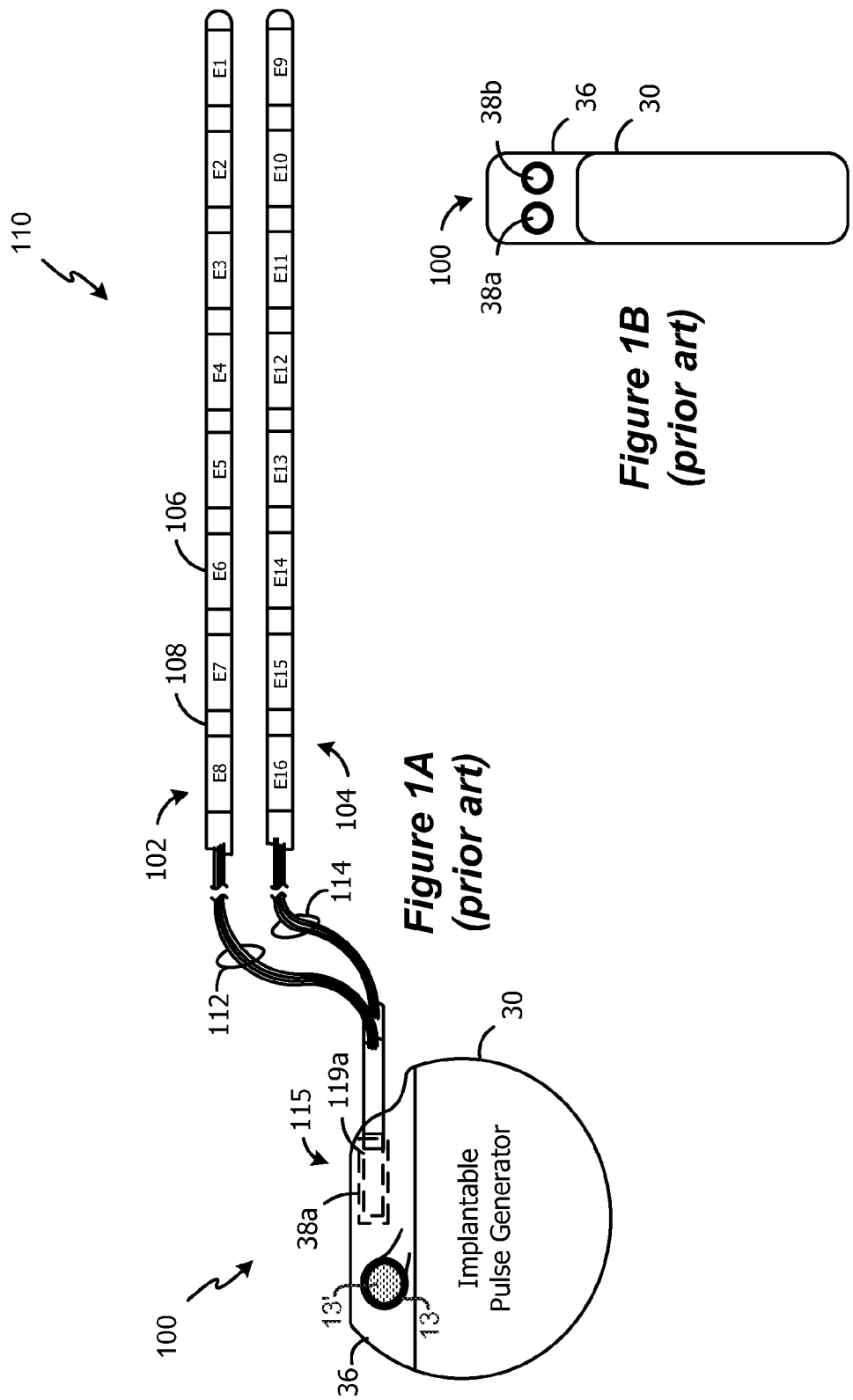
Figure 2:
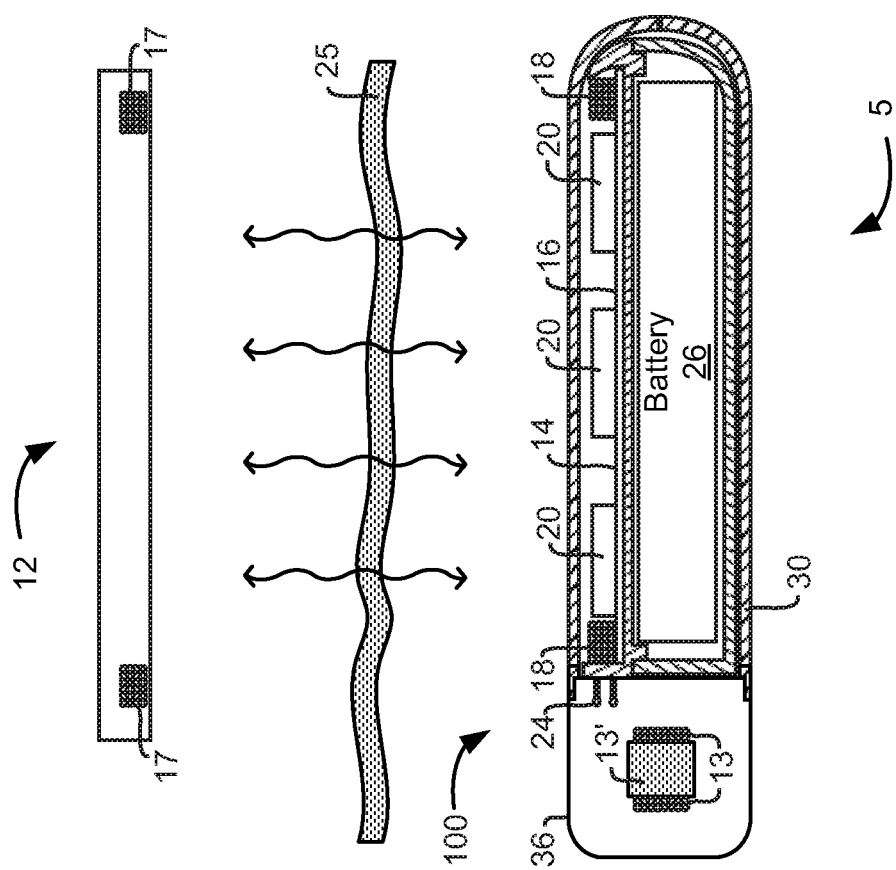
FIG. 2 shows wireless communication of data between an external controller and an IPG.
Figure 3:
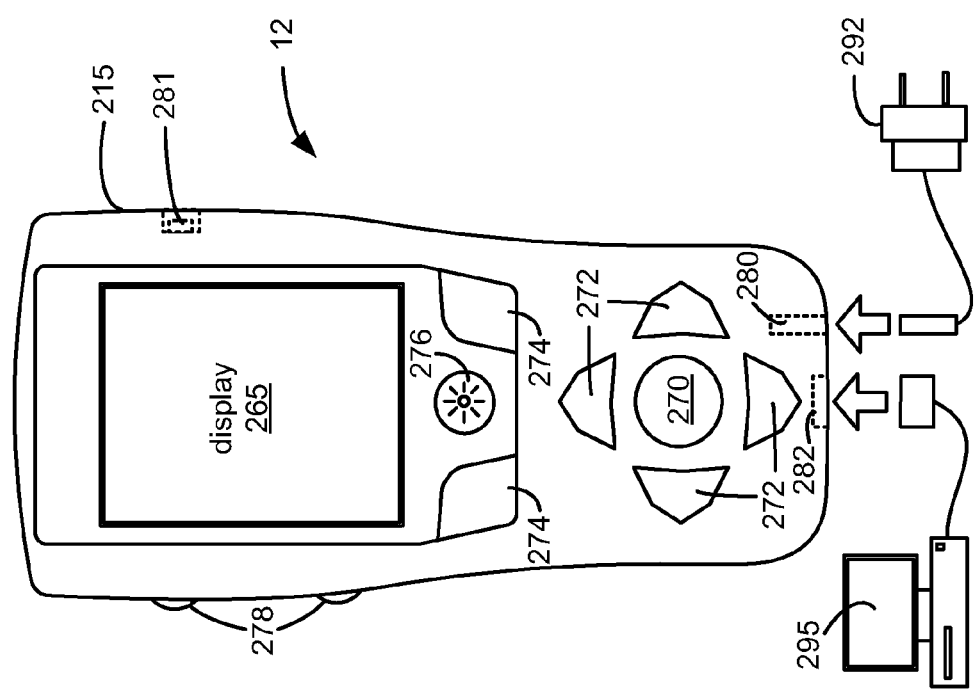
FIG. 3 shows a typical external controller of the prior art.
Figure 4:
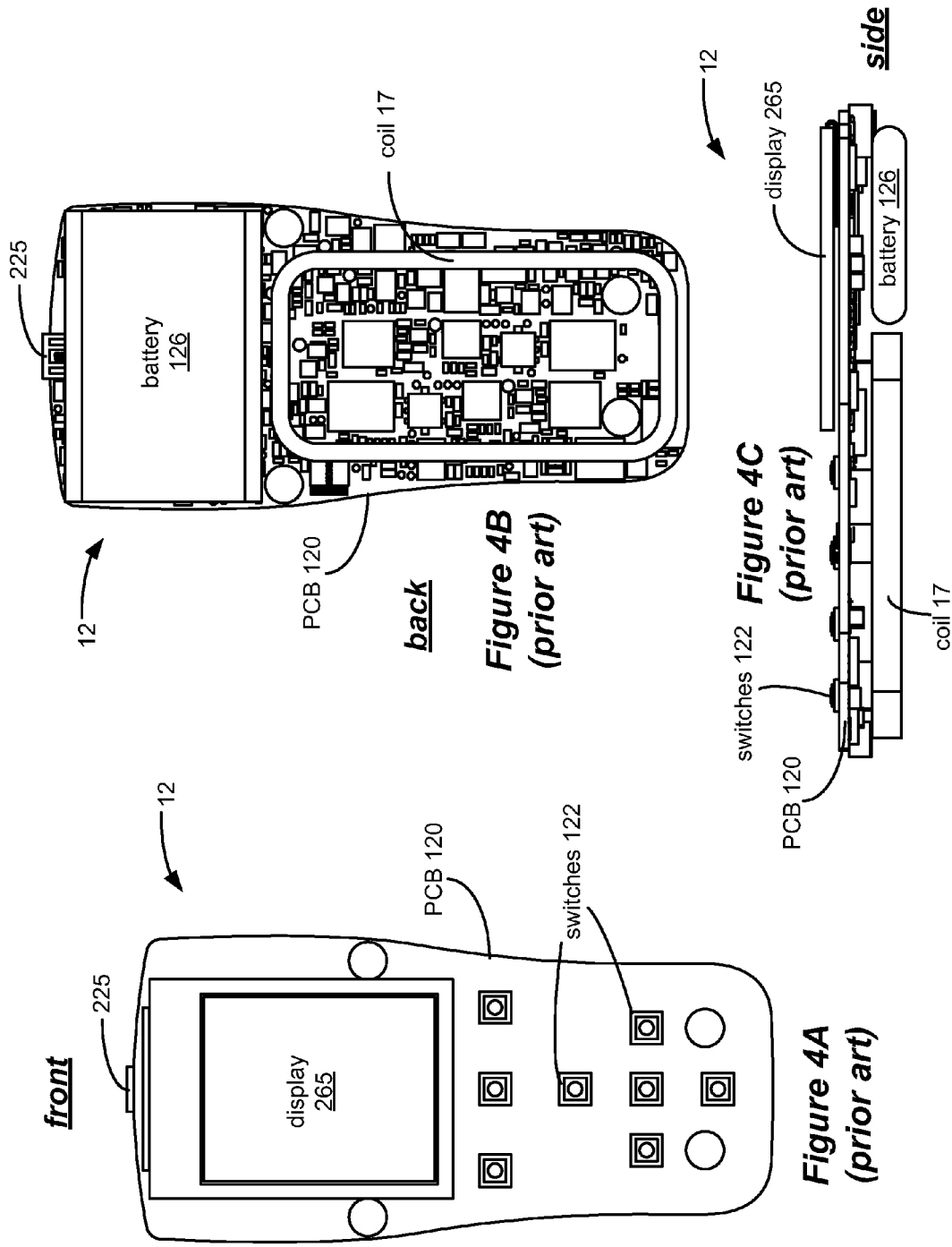
FIGS. 4A-4C show from different viewpoints the internal components of the external controller of FIG. 3, including its incorporation of a traditional wound communication coil.
Figure 5:
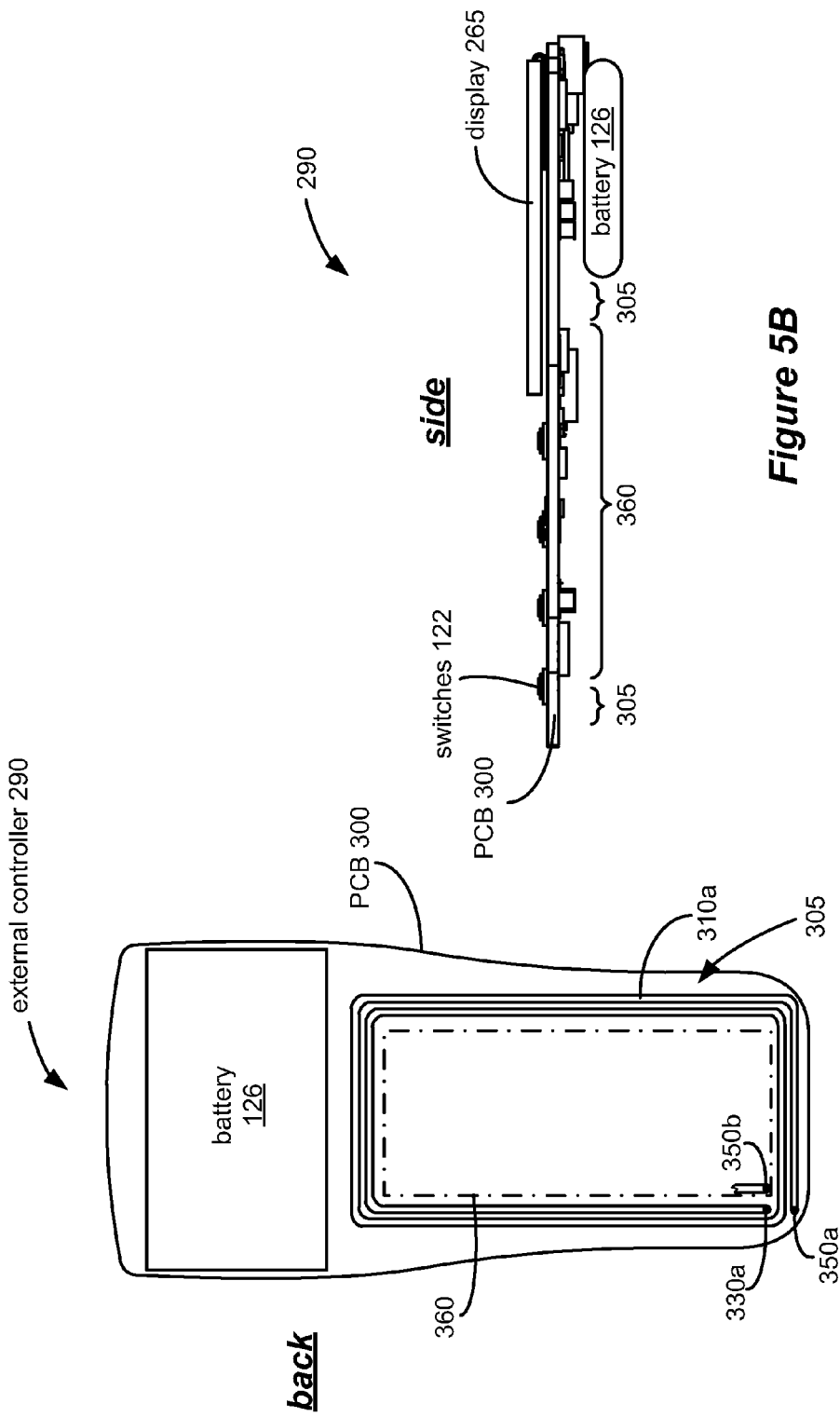
FIGS. 5A and 5B show from different viewpoints the internal components of the improved external controller of the invention having a PCB communication coil from different view points.

One embodiment of an improved external controller 290 is illustrated in FIGS. 5A and 5B. Like corresponding FIGS. 4B and 4C, FIGS. 5A and 5B show back and side views of the external controller 290 with its housing removed. (The housing, user interface, and the front side, as depicted in FIGS. 3 and 4A, could be the same as in the prior art, and thus such aspects are not reiterated here). Manufacture of the improved external controller 290, like external controller 12 described earlier, centers around a printed circuit board (PCB) 300. However, unlike the PCB 120 used in the external controller 12 of the prior art, the PCB 300 in the improved external controller 290 includes a communication coil 305. This communication coil 305 is fabricated using traces on the PCB 300, as opposed to using copper wire windings as was used for communication coils 17 in the prior art. Such PCB traces will be explained in more detail later.

Using PCB conductors for the communication coil 305 solves significant problems with the design and manufacturing of external controllers. As mentioned earlier, it is generally difficult and unreliable to build traditional copper-wire communication coils 17. Moreover, special mounting steps must be used to affix such traditional copper-wire coils to their PCBs. By contrast, the traces for the coil 305 are formed just as are other traces on the PCB 300, therefore obviating the need for a separate manufacturing process to make the coil. Coiled traces on the PCB 300 are easily made with good precision and repeatability, alleviating concerns about variability of the resistance and inductance of the coil during manufacture. Testing of such values, if necessary, is easily accomplished during otherwise standard reliability testing of the PCB. Such traces are reliable by virtue of the use of established PCB formation techniques, and are not prone to the sorts of mechanical failure modes (e.g., shorted turns) experienced by traditional windings in the prior art, nor are they sensitive to shock, vibration, temperature fluctuations, and/or humidity. PCB coils are also well suited for mass production of many thousands of units.

Figure 6:
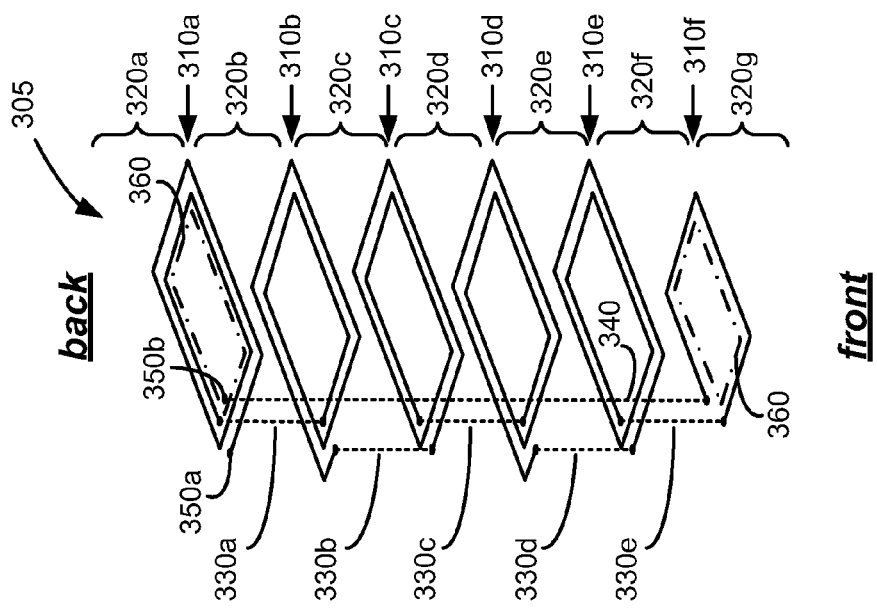
FIG. 6 shows in schematic form the multilayer PCB communication coil used in the improved external controller.

In a preferred implementation, the PCB 300 is a multilayer PCB, having traces at a plurality of layers of the PCB. Such multilevel PCBs are ubiquitous in the electronic industry, and are favored to maximize flexibility in interconnecting the various components (e.g., integrated circuits) mounted to the PCB. An exemplary coil 305 formed using a multilayer PCB 300 is shown in FIG. 6. As shown the coil 305 is composed in a PCB 300 having six layers: a layer 310a proximate the back side; layer 310f proximate the front side; and four layers 310b-e in between. One skilled in the art will understand that between each of the layers 310 reside layers of insulation 320a-320g. However, these layers of insulation are not shown in FIG. 6 so that the coil structure can be better appreciated in three dimensions. Although illustrated as comprising six layers 310a-f, this number is merely exemplary and could comprise different numbers of layers, from one to much higher numbers. The number of layers chosen can depend on the inductance required by the coil 305, as will be explained further below. If a sufficient number of turns can be provided, the coil 305 can be constructed at a single layer of traces. Any standard material for the PCB 300 is acceptable, including industry-standard FR4-based PCBs.

The coil 305 as shown in FIG. 6 has two terminals 350a and 350b at either end which allows the coil to be coupled to appropriate communication circuitry 360 on the back side of the PCB. Although generically illustrated in the Figures, communication circuitry 360 comprises circuitry for compiling a therapy program for the IPG 100, which program is eventually broadcast to the IPG as a wireless signal by the communication circuitry by activating the coil 305. Starting from terminal 350a, it can be seen that the traces at layer 310a make two counter-clockwise turns that spiral inwardly. At this point, the traces meet with a via 330a which connects traces at layer 310a with traces at layer 310b. Such inter-layer vias, and how to manufacture them, are well known and require no further explanation. Thereafter, the traces at layer 310b again make two counter-clockwise turns, although this time spiraling outwardly. Traces 310b then meets with the next via 330b to connect with traces at layer 310c, which traces at layer 310c again make two counter-clockwise turns that spiral inwardly, and so on. The overall effect is a coil 305 that is essentially similar to a traditional copper winding, but built with more precision and reliability. It should be understood that the illustrated coil 305 in FIG. 6 is but one way to make a suitable PCB coil 305.

At (front) layer 310f notice that the turns stop short of a full two turns to allow a via 340 to route that end of the coil back to (back) layer 310a at terminal 350b. Because the turns stop short, terminal 350b is within the turns at layer 310a. This makes it possible to connect the coil 305 to external controller circuitry 360 residing on the PCB 300 within the turns at layer 310a, as best illustrated in FIG. 5A. In a preferred implementation, the coil 350 is made to go around or encompass at least some of the external controller's circuitry 360, which would include standard circuitry such as a microcontroller, communication circuitry for interaction with the coil, etc. While such external controller circuitry 360 may occur primarily on the backside of the PCB 300 as shown in the side view of FIG. 5B, some of this circuitry 360 (such as the switches 122) may also occur on the front side, as shown in FIG. 6. While it is not strictly necessary that all of the external controller circuitry 360 reside within the coil 305, such an arrangement is preferred: if there is at least a portion of circuitry 360 outside of the coil 305 on the PCB 300, it may be difficult to couple such circuitry to the remaining circuitry 360 inside the coil, because the turns of the coil prohibit interconnectivity with at least some layers. Having said this, at least portions of external controller circuitry 360 can also reside outside of the coil 305 on the PCB 300. For example, and referring to FIG. 5B, note that the battery 126 and display 265 can be located outside of the coil 305. To connect such circuitry to other circuitry 360 inside of the coil, it may be advantageous not to have full turns of coil at the outermost layer 310a to allow for interconnectivity.

It is preferred that the PCB coil 305 remain substantially unobstructed by structures that might interfere with the magnetic fields it produces. For example, battery 126 could provide such interference, and therefore the battery 126 preferably does not overhang the coil 305. Alternatively, the coil 305 cold go around the battery 126, i.e., around the entire periphery of the PCB 300, to avoid such interference.

When used in an external controller 290 for an implantable medical device system, a suitable coil 305 may have two to four turns per layer on a six-layered PCB 300, i.e., between 12-24 turns total. The traces comprising the coil may have a width of about 1-2 millimeters, and each turn (if generally constructed as a square as shown in FIG. 5A) can encompass about a 4 centimeter by 6 centimeter area. So constructed, the inductance of the resulting coil 305 may be approximately 50 microhenries. At the communication frequencies contemplated for the illustrated implantable medical device system (e.g., 50-500 kHz), such high inductance is desirable, as explained further below. The inductance can be further increased by increasing the area of the coil, increasing the number of turns at each layer, or increasing the number of layers. Increasing the trace width and thickness (amount of copper) reduces resistance and increases the quality factor "Q" of the coil, which improves efficiency. For a telemetry communications coil, a Q factor of 10 is sufficient to provide the bandwidth required for typical telemetry data rates. A higher Q coil is more efficient, but reduces the bandwidth. Generally speaking, a PCB coil can have higher power handling capability due to its potentially larger surface area.

Because the disclosed PCB coil communicates via magnetically coupling, it does not operate as a typical communications antenna (e.g., microstrip or patch antennas), which might be found in cellular telephones for example and which typically operates at much higher frequencies. Instead, the disclosed PCB coils produce a magnetic field, which magnetic field carries the communication by magnetic inductive coupling in the receiving coil. Use of a PCB coil for communications is believed to be novel in an implantable medical device system. Fortunately, a PCB coil will support communication at the relatively low frequencies (sub-4 MHz) dictated by the human body environment discussed above, and so is well suited for use in an implantable medical device system. A traditional communication antenna operating at sub-4 MHz, by contrast, is not understood to be implementable on a PCB, because sub 10-MHz radiation would comprise a wavelength of many meters, which is far too large to be accommodated on a typical printed circuit board. In other words, one could not merely modify a traditional PCB communication antenna to operate at sub-4 MHz in an implantable medical device system.

Maximizing the PCB coil 305's inductance is generally beneficial in the medical implantable device communication system illustrated. This is because communications between the external controller 290 and the IPG 100 will generally not exceed 4 MHz, and instead will typically range from 50 to 500 kHz. This is because the body of a human patient in which the IPG 100 is implanted will generally attenuate electrical fields exceeding 4 MHz. Such attenuation is of course not desirable because if too severe it will affect signal strengths or require higher battery powers to compensate for such loss of signal strength. Communications in the sub-10 MHz range will require use of a coil with a relatively high inductance, e.g., 50 microhenries as stated above.

As well as providing improved reliability when compared to traditional wound coils, the external controller 290 also benefits from the slimmer profile that the PCB coil 305 provides. The thinner nature of the resulting circuitry with the use of the PCB coil 305 is evident when one compares FIG. 5B with FIG. 4C.

Although the invention has been illustrated in the context of an external controller used to send and receive data to and from an IPG 100, a PCB coil could also be used to replace the coil used in an external charger used to wirelessly recharge the battery within the IPG. An example of an external charger is provided in U.S. patent application Ser. No. 11/460,955, filed Jul. 28, 2006, which is incorporated herein in its entirety. As one reviewing that patent application will understand, an external charger activates a charging coil to broadcast a wireless signal comprising a magnetic field which transmits power to the charge coil in the IPG 100, which signal can be rectified and used to charge the battery in the IPG or otherwise power the IPG.

Other patent applications assigned to the Applicant discuss benefits of an external controller or external charge having at least two orthogonal coils. See, e.g., U.S. patent application Ser. No. 11/853,624, filed Sep. 11, 2007; U.S. patent application Ser. No. 11/622,395, filed Jan. 11, 2007, both of which are hereby incorporated herein by reference. The PCB coils disclosed herein can, in accordance with these patent applications, be placed orthogonally to improve the directionality of the communication. This can be achieved by either by two or more rigid PCB coils that attach orthogonally. Additionally, the two PCB coil can be incorporated into a single substrate that is flexible, such that the substrate is bendable to align the two or more coils placed on it orthogonally to each other.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
   an external device for sending a wireless signal to an implantable medical device, comprising:
   a hand-held housing;
   a printed circuit board (PCB) within the housing, the PCB having a plurality of layers of traces;
   a first coil for broadcasting via magnetic coupling the wireless signal to the implantable medical device, wherein the first coil comprises a plurality of turns in the traces in the plurality of layers of the PCB, wherein a via between adjacent layers directly connects the plurality of turns in the adjacent layers;
   external device circuitry mounted to the PCB and for activating the first coil to transmit the wireless signal, wherein the external device circuitry is within the first coil; and
   a battery within the housing, wherein the battery is outside of and does not overhang the coil; and
   an implantable medical device, wherein the implantable medical device comprises a second coil for receipt of the wireless signal broadcast from the first coil.

2. The system of claim 1, wherein the wireless signal comprises data.

3. The system of claim 1, wherein the wireless signal comprises power.

4. The system of claim 1, wherein the wireless signal comprises a signal at a frequency less than 10 MHz.

5. The system of claim 1, wherein each of the plurality of turns in each layer are wound in a counterclockwise direction, and wherein the plurality of turns alternate at successive layers between being wound inwardly and outwardly.

6. The system of claim 1, wherein the external device circuitry comprises communication circuitry for interaction with the first coil.

7. The system of claim 1, wherein the external device circuitry comprises a microcontroller.

* * * * *